US 6,423,231 B1

(12) United States Patent
Collins et al.

(10) Patent No.: US 6,423,231 B1
(45) Date of Patent: Jul. 23, 2002

(54) NON-ISOSMOTIC DIAFILTRATION SYSTEM (75) Inventors: Gregory R. Collins, Monroe; Edward C. Spence, Bronx, both of NY (US)

(73) Assignee: Nephros, Inc., New York, NY (US)

(*) Notice: Subject to any disclaimer, the term of this patent is extended or adjusted under 35 U.S.C. 154(b) by 0 days.

(21) Appl. No.: 09/485,782

(22) PCT Filed: Oct. 29, 1999

(86) PCT No.: PCT/US99/25804
§ 371 (c)(1),
(2), (4) Date: Mar. 1, 2000

(87) PCT Pub. No.: WO00/25902
PCT Pub. Date: May 11, 2000

Related U.S. Application Data (60) Provisional application No. 60/106,322, filed on Oct. 30, 1998.

(51) Int. Cl.⁷ .................. B01D 61/24; B01D 61/26; B01D 61/28; B01D 61/32; A61M 1/34
(52) U.S. Cl. .................. 210/646; 210/97; 210/143; 210/252; 210/321.6; 210/321.71; 210/321.72; 210/323.2; 210/434; 210/645; 210/647; 210/929; 604/4.01; 604/5.04
(58) Field of Search ............... 210/87, 90, 97, 210/143, 195.2, 252, 321.6, 321.72, 321.71, 323.2, 434, 645, 646, 647, 929; 604/4.01, 5.04

(56) References Cited

U.S. PATENT DOCUMENTS

| 3,579,441 A | 5/1971 | Brown |
| 3,744,636 A * | 7/1973 | Commarmoot ............. 210/180 |
| 3,878,095 A | 4/1975 | Frasier et al. ................ 210/87 |
| 3,946,731 A | 3/1976 | Lichtenstein ................. 128/214 |
| 4,038,190 A | 7/1977 | Baudet et al. .............. 210/321 |
| 4,118,314 A | 10/1978 | Yoshida ..................... 210/22 |
| 4,381,999 A | 5/1983 | Boucher et al. ............ 210/637 |
| 4,498,990 A | 2/1985 | Shaldon et al. ............ 210/637 |
| 4,647,378 A | 3/1987 | Minami ...................... 210/646 |
| 4,702,829 A | 10/1987 | Polaschegg et al. ..... 210/195.2 |
| 4,708,802 A | 11/1987 | Rath et al. ................. 210/641 |
| 4,722,798 A | 2/1988 | Goss ......................... 210/646 |
| 4,770,769 A | 9/1988 | Schael ...................... 210/96.2 |
| 4,784,495 A | 11/1988 | Jonsson et al. ............ 366/151 |
| 4,834,888 A | 5/1989 | Polaschegg ................ 210/646 |
| 4,861,485 A | 8/1989 | Fecondini .................. 210/641 |
| 5,011,607 A | 4/1991 | Shinzato .................... 210/637 |
| 5,069,788 A | 12/1991 | Radovich et al. ........ 210/321.8 |
| 5,075,003 A | 12/1991 | Aoyagi .................... 210/321.8 |
| 5,178,763 A | 1/1993 | Delaunay ................... 210/644 |

(List continued on next page.)

FOREIGN PATENT DOCUMENTS

| EP | 0076422 | 4/1983 |
| EP | 0 516 152 B1 | 12/1992 |
| EP | 0 960 624 A2 | 12/1999 |
| WO | WO 98 30258 | 7/1998 |
| WO | WO 98/35710 | 8/1998 |

OTHER PUBLICATIONS

Technical Aspects of High–Flux Hemodiafiltration for Adequate Short (Under 2 Hours) Treatment (pp. 377–380) (undated).

Hemodiafiltration with On–Line Production of Substitution Fluid: Long–Term Safety and Quantitative Assessment of Efficacy (pp. 13–21) Contrib Nephrol. Basel, Karger, 1994, vol. 108. pp. 12–22.

(List continued on next page.)

Primary Examiner—John Kim
(74) Attorney, Agent, or Firm—Darby & Darby (57) ABSTRACT A method of hemodiafiltration including the steps of supplying a blood inflow, diafiltering the blood inflow using a first non-isosmotic dialysate fluid to provide a partially diafiltered blood outflow, mixing the partially diafiltered blood outflow with a substitution fluid to provide a blood/substitution fluid mixture, and diafiltering the blood/substitution fluid mixture using a second non-isosmotic dialysate fluid.

23 Claims, 3 Drawing Sheets

U.S. PATENT DOCUMENTS

| | | |
|---|---|---|
| 5,194,157 A | 3/1993 | Ghezzi et al. ............... 210/646 |
| 5,244,568 A | 9/1993 | Lindsay et al. ............... 218/87 |
| 5,318,750 A | 6/1994 | Lascombes .................. 422/81 |
| 5,431,811 A | 7/1995 | Tusini et al. .................. 210/90 |
| 5,476,592 A | 12/1995 | Simard ....................... 210/651 |
| 5,487,827 A | 1/1996 | Peterson et al. ............... 210/87 |
| 5,511,875 A | 4/1996 | Jonsson et al. ............. 366/136 |
| 5,660,722 A | 8/1997 | Nederlof ...................... 210/90 |
| 5,690,831 A | 11/1997 | Kenley et al. ............... 210/646 |
| 5,702,597 A | 12/1997 | Chevallet et al. ........... 210/195 |
| 5,711,883 A | 1/1998 | Folden et al. ............... 210/646 |
| 5,725,775 A | 3/1998 | Bene et al. .................. 210/646 |
| 5,744,042 A | 4/1998 | Stange et al. ............... 210/645 |
| 5,808,181 A | 9/1998 | Wamsiedler et al. ........... 73/38 |
| 5,846,419 A | 12/1998 | Nederlof .................. 210/323.1 |
| 5,882,516 A | 3/1999 | Gross et al. ............. 210/321.6 |

OTHER PUBLICATIONS

Albertini, B. von et al.: High–Flux Hemodiafiltration: Under Six Hours/Week Treatment. vol. XXX Trans Am Soc Artif Intern Organs 1984, pp. 227–230.

Albertini, B. von et al.: Performance Characteristics of High–Flux Hemodiafiltration. Abstract of $2^{nd}$ Annual Workshop of the International Society of Hemofiltration. Blood Purification 2:44–64 (1984).

Fremont et al.: Evaluation of Short–Time Hemofiltration. Abstract from $2^{nd}$ Annual Workshop of the International Society of Hemofiltration. Blood Purification 2:44–64 (1984).

Ghezzi, P.M. et al.: Hemodiafiltration Without Replacement Fluid. ASAIO Journal 1992.

Ghezzi, P.M et al.: Use of the ultrafiltrate obtained in two–chamber (PFD) hemodiafiltration as replacement fluid. The International Journal of Artificial Organs/vol. 14/No. 6, 1991/pp. 327–334.

Ghezzi et al.: Extracorporeal Blood Purification in Uremic Patients by a Separate Convective–Diffusive System. Abstract from $2^{nd}$ Annual Workshop of the International Society of Hemofiltration. Blood Purification 2:44–64 (1984).

Kim, Sung–Teh: Characteristics of Protein removal in Hemodifiltration. Maeda K. Shinzato T (eds): Effective Hemodiafiltration:New Methods. Contrib Nephrol. Baser, Karger, 1994, vol. 108, pp. 23–37.

Marangoni, Roberto et al.: Short Time Treatment with High–Efficiency Paired Filtration Dialysis for Chronic Renal Failure. Artificial Organs 16(6):547–552, Blackwell Scientific Publications, Inc., Boston 1992 International Society for Artificial Organs.

Ono, Masataka et al.: Comparison of Types of On–Line Hemodiafiltration from the Standpoint of Low–Molecular–Weight Protein Removal. Maeda K. Shinzato T (eds): Effective Hemodiafiltration:New Methods. Contrib Nephrol. Baser, Karger, 1994, vol. 108, pp. 38–45.

Polaschegg et al.: Hemodialysis Machines and Monitors, pp. 354–358 (undated).

Ronco, C. et al.: Technical and Clinical Evaluation of Different Short, Highly Efficient Dialysis Techniques. Contr. Nephrol., vo. 61, pp. 46–68 (Karger, Basel 1988).

Ronco, C. et al.: Comparison of four different short dialysis techniques. The International Journal of Artificial Organs/vol. 11/No. 3, 1988/pp. 169–174.

Ronco, C. et al.: Paired Filtration Dialysis: Studies of Efficiency, Flow Dynamics and Hydraulic Properties of the System. Blood Purif 1990; 8:126–140.

Rotellar, Emilio et al.: Large–Surface Hemodialysis. Artificial Organs 10(5):387–396, Raven Press, New York, 1986 International Society for Artificial Organs.

Sanz–Moreno, C. et al.: Hemodiafiltration in Two Chambers Without Replacement Fluid: A Clinical Study. Artificial Organs 19(5):407–410 Blackwell Scientific Publications, Inc., Boston 1995 International Society for Artificial Organs.

Shaldon, S. et al.: Mixed Hemofiltration (MHF): 18 Months Experience With Ultrashort Treatment Time. vol. XXVII Trans Am Soc Artif Intern Organs 1981, pp. 610–612.

Shinaberger, James H. et al.: 16: Short Treatment, Techniques for shortened treatment pp. 372–375.

Shinzato, T et al.: Infusion–Free Hemodiafiltration: Simultaneous Hemofiltration and Dialysis with No Need for Infusion Fluid Artificial Organs 1982; 6: 453–456.

Sternby, Jan: A Decade of Experience with On–Line Hemofiltration/Hemodiafiltration. Maeda K. Shinzato T (eds): Effective Hemodiafiltration:New Methods. Contrib Nephrol. Baser, Karger, 1994, vol. 108, pp. 1–11.

Vanholder et al.: In vivo solute elimination of paired filtration dialysis. The International Journal of Artificial Organs/vol. 14/No. 1, 1991/pp. 23–27.

Zucchelli, P. et al.: Paired Filtration Dialysis: Optimizing Depurative Efficiency with Separate Convection and Diffusion Processes. Nephron 1990; 56:166–173.

* cited by examiner

NON-ISOSMOTIC DIAFILTRATION SYSTEM

This application claims the benefit of provisional application 60/106,322 filed Oct. 30, 1998.

FIELD OF THE INVENTION

The present invention relates to blood cleansing in general and, more particularly, to diafiltration systems.

BACKGROUND OF THE INVENTION

Hemodiafiltration combines standard dialysis and hemofiltration into one process, whereby a dialyzer cartridge containing a high flux membrane is used to remove substances from the blood both by diffusion and by convection. The removal of substances by diffusion is accomplished by establishing a concentration gradient across a semi-permeable membrane by flowing a dialysate solution on one side of the membrane while simultaneously flowing blood on the opposite side of the membrane. To enhance removal of substances using hemodiafiltration, a substitution fluid is continuously added to the blood either prior to the dialyzer cartridge (pre-dilution) or after the dialyzer cartridge (post-dilution). An amount equal to that of the substitution fluid is then ultrafiltered across the dialyzer cartridge membrane carrying with it additional solutes.

Substitution fluid is usually purchased as a sterile/non-pyrogenic fluid contained in large flexible bags or is produced by on-line filtration of a non-sterile dialysate through a suitable filter cartridge rendering it sterile and non-pyrogenic. Such on-line production of substitution fluid is described, inter alia, in D. Limido et al., "Clinical Evaluation of AK-100 ULTRA for Predilution HF with On-Line Prepared Bicarbonate Substitution Fluid. Comparison with HD and Acetate Postdilution HF", *International Journal of Artificial Organs*, Vol. 20, No.3 (1997), pp. 153–157.

In general, hemodiafiltration schemes use a single dialyzer cartridge containing a high flux semi-permeable membrane. Such a scheme is described, for example, in P. Ahrenholz et al., "On-Line Hemodiafiltration with Pre- and Postdilution: A comparison of Efficiency", *International Journal of Artificial Organs*, Vol. 20, No.2 (1997), pp 81–90 ("Ahrenholz et al."). Substitution fluid is introduced into the blood stream either in a pre-dilution mode or in a post-dilution mode relative to the dialyzer cartridge. The preferred mode for maximal removal of both small and large substances from blood is the post-dilution mode, which achieves the highest concentration gradient between the blood and the dialysate fluid. In a typical pre-dilution mode with on-line generation of the substitution fluid, however, the bloodside concentration is lowered relative to the dialysate fluid. As a result, removal (or clearance) of substances can decrease, as described in Ahrenholz et al. This is particularly true for smaller molecules like urea, whereby mass transport is driven more by the diffusion process than by the convection process.

A hemodiafiltration scheme using first and second dialyzer cartridges is described in J. H. Miller et al., "Technical Aspects of High-Flux Hemodiafiltration for Adequate Short (Under 2 Hours) Treatment", Transactions of American Society of Artificial Internal Organs (1984), pp. 377–380. In this scheme, the substitution fluid is reverse-filtered through a membrane of the second dialyzer cartridge with simultaneous filtration of fluid across a membrane in the first dialyzer cartridge. Counter-current flow of dialysate occurs at both cartridges.

Certain trade-offs exist with respect to removal of different size molecules when comparing pre-dilution diafiltration and post-dilution diafiltration using a single dialyzer cartridge. For example, with on-line pre-dilution diafiltration, one can achieve higher convective filtration rates (compared to on-line post-dilution diafiltration) to enhance removal of large molecules, however, this comes at the expense of reducing the removal of small molecules like urea and creatinine. In on-line post-dilution diafiltration, however, only a limited amount of fluid can be filtered from the blood as it passes through the dialyzer cartridge. The filterable amount is dependent upon several factors, including blood flow rate, blood hematocrit and blood protein concentration. Typically, the filterable amount is 20% to 30% of the incoming blood flow, depending on blood flow rate. For example, at a blood flow rate of 300 ml/min, the filterable amount is limited to about 90 ml/min. Additionally, in on-line pre-dilution or post-dilution diafiltration, there is some loss in clearance due to the lower dialysate flow rate through the diafilter cartridge. For example, at a nominal dialysate flow of 500 ml/min, when 100 ml/min is used as an on-line source of substitution fluid, the resultant dialysate flow into the diafilter cartridge is 400 ml/min.

SUMMARY OF THE INVENTION

It is an object of the present invention to provide a hemodiafiltration method and a device which overcome the limitations associated with convection filtration in existing on-line post-dilution schemes. It is also an object of the present invention to reduce the loss of small molecule clearance associated with on-line pre-dilution diafiltration using a single dialyzer cartridge. In accordance with the present invention, clearance is improved by introducing a non-isosmotic fluid to the dialysate fluid stream and optionally to the substitution fluid stream.

The present invention may be embodied in an improved dialysis machine, e.g., a dialysis machine which is adapted to perform improved hemodiafiltration in accordance with the invention. Alternatively, the hemodiafiltration device of the present invention may be embodied in an "add-on" system which may be used in conjunction with a standard UF controlled dialysis machine to perform improved hemodiafiltration.

A hemodiafiltration device in accordance with an embodiment of the present invention includes at least one dialyzer (e.g., a dialyzer cartridge) for diafiltration, at least one sterility filter (e.g., a sterility filter cartridge) for generating a sterile substitution fluid, a non-isosmotic fluid supply, and a control unit which controls fluid inputs and outputs between the at least one dialyzer, the at least one sterility filter cartridge, the non-isosmotic fluid supply and the dialysis machine.

The dialyzer may contain a semi-permeable membrane which may be embedded within a jacket or housing of a dialyzer cartridge. The membrane separates the dialyzer into a blood compartment and a dialysate compartment. In an embodiment of the present invention, at least first and second dialyzers are used to carry out the diafiltration process. The first and second dialyzers may include first and second dialyzer cartridges or a single cartridge having first and second dialyzer sections. The at least one sterility filter may contain semi-permeable membranes and may be used to remove bacteria, endotoxins, and other particulate from the dialysate, thereby generating a suitable substitution fluid stream on-line. The control unit may contain various pumps, pressure monitoring devices, valves, electronic components, connector fittings, tubing, etc., as required in order to coordinate the operation of the other system components.

Blood enters the bloodside compartment of the first dialyzer, whereby some plasma water is filtered across the semi-permeable membrane into the adjacent dialysate compartment. As the blood leaves the first dialyzer, substitution fluid is added to the blood at a rate higher than the rate at which plasma water is filtered out of the first dialyzer. In accordance with an embodiment of the present invention, the substitution fluid may include a non-isosmotic substitution fluid.

The diluted blood then enters the bloodside compartment of the second dialyzer, whereby additional plasma water (equal to the excess amount of substitution fluid) is filtered across the semi-permeable membrane and into the adjacent dialysate compartment. In this manner, the substitution fluid acts as a post-dilution fluid relative to the first dialyzer as well as a pre-dilution fluid relative to the second dialyzer.

An advantage of this process is that a gain in clearance of small molecular weight substances in the first dialyzer overshadows a loss in clearance of small molecular weight substances due to the dilution of blood concentration entering the second dialyzer. Further, clearance of larger molecular weight substances is enhanced considerably, because the total filtration level of plasma water is practically doubled (e.g. 40% to 80% of the incoming blood flow rate may be filtered) compared to filtration using a single dialyzer operating in a post-dilution mode.

The dialysate fluid may be generated by the dialysis machine. Preparation of the dialysate solution may include mixing of water with dialysate concentrate. Using a water preparation module, a supply of water may be pre-treated, e.g., by heating and/or degassing or using any other pre-treatment method known in the art. A dialysate preparation module, as is known in the art, may be used to supply dialysate concentrate to obtain suitable proportioning of dialysate to water.

When two dialyzers are used, the dialysate fluid may enter the second dialyzer cartridge and run counter-parallel to the blood flow direction. In accordance with an embodiment of the present invention, the dialysate preparation module produces non-isosmotic or isosmotic dialysate fluid. The dialysate fluid acts to provide a concentration gradient against the bloodside fluid thereby facilitating the diffusion of solutes across the semi-permeable membrane. As the dialysate traverses through the dialysate compartment, the dialysate flow rate increases due to plasma water filtering across into the dialysate compartment as mentioned above. Upon exiting the second dialyzer cartridge, the dialysate fluid may be pumped into the first dialyzer cartridge, again running counter-parallel to the bloodside fluid. At this point, a non-isosmotic dialysate fluid may be added to the dialysate fluid, resulting in fluid which is either hypertonic or hypotonic relative to the blood. The addition of this fluid may have the following effects: (a) an increase in the overall dialysate flow results in a reduction of the dialysate side-mass transport resistance; (b) a reduction in the dialysate inlet solute concentration prior to entering the first dialyzer cartridge results in an increase of the concentration gradient across the semi-permeable membrane; (c) a fluid shift across the red blood cell membrane further enhances transport of solutes out of the red blood cells; and (d) larger molecules sieved by the red blood cell membrane are trapped in the plasma water space thus increasing their concentration gradient relative to the dialysate. In some embodiments of the invention, pre-treated water is used as the non-isosmotic fluid added to the dialysate fluid. This may have the added benefit of increasing dialysate flow without increasing costs associated with the amount of dialysate concentrate being used.

The dialysate flow rate increases as it traverses through the dialysate compartment again, due to filtration of plasma water across the semi-permeable membrane. Upon exiting the dialyzer cartridges, the used dialysate is transported back to the dialysis machine. A dialysate pump may be placed between the first and second dialyzers. The pump may be used to control the relative amount of plasma water filtered across the membranes of the two dialyzers.

Preparation of the sterile/non-pyrogenic substitution fluid may be performed by drawing a portion of fresh dialysate solution from a dialysate inlet line and pumping it through the sterile filter cartridge. Water from the water preparation module may be added to the dialysate, such that the substitution fluid becomes hypotonic before it is infused into the blood stream. The sterile filter cartridge may perform multiple filtration of the dialysate solution, e.g., using a plurality of filtration cartridges or a plurality of filtration sections in a single cartridge, before introducing the dialysate into the blood stream as substitution fluid. This enhances safety, e.g., should one of the filters fail during treatment.

To ensure that the blood does not become diluted or over-concentrated as it passes through the dialyzer cartridges, control of filtration may be accomplished by use of two independent fluid balancing systems and a separate UF pump. A main balance system may regulate the overall dialysate flows, while a secondary balance system may be used to balance dialysate flows that are offset by the addition of a second fluid stream to the dialysate circuit as part of the non-isosmotic flow streams. To ensure that the blood being cleaned returns substantially to its original osmotic state before going back to the patient, the primary dialysate fluid may be isotonic, slightly hypertonic, or slightly hypotonic, depending on the nature of the second dialysate fluid. Pressures may be monitored both on the bloodside and dialysate side of each dialyzer cartridge as a means to determine transmembrane pressure (TMP) across each of the dialyzers.

BRIEF DESCRIPTION OF THE DRAWINGS

The present invention will be understood and appreciated more fully from the following detailed description of embodiments of the present invention, taken in conjunction with the accompanying drawing in which.

DETAILED DESCRIPTION OF PREFERRED EMBODIMENTS

The hemodiafiltration method and device of the present invention will be described below in the context of a stand-alone dialysis/hemodiafiltration machine. It should be appreciated, however, that the hemodiafiltration method and device of the present invention can also be embodied in an add-on type system used in conjunction with an existing UF controlled dialysis machine.

In an embodiment of the present invention, as described below with reference to the drawing, the hemodiafiltration device includes first and second dialyzer cartridges. Alternatively, a single cartridge having first and second, separate, dialyzer sections may be used.

The hemodiafiltration device further includes at least one sterility filter, which may contain semi-permeable membranes for removing bacteria, endotoxins, and other particulate from the dialysate, thereby to generate a suitable substitution fluid stream on-line. The device also includes a fluid module to coordinate between different elements of the system. The fluid module contains various pumps, pressure monitoring devices, valves, electronic components, connector fittings, tubing, etc., as required in order to coordinate the operation of the other system components.

In accordance with an embodiment of the present invention, preparation of dialysate solution includes mixing of water with dialysate concentrate. Using a water preparation module, a supply of water may be pre-treated, e.g., by heating and/or degassing or using any other pre-treatment method known in the art. A dialysate preparation module may be used to supply a predetermined amount of dialysate concentrate to obtain a suitable proportioning of dialysate to water.

When two dialyzers are used, the dialysate fluid may enter the second dialyzer cartridge and run counter-parallel to the blood flow direction. In accordance with an embodiment of the present invention, the dialysate preparation module produces non-isosmotic dialysate fluid. The dialysate fluid acts to provide a concentration gradient against the bloodside fluid thereby facilitating the diffusion of solutes across the semi-permeable membrane. As the dialysate traverses through the dialysate compartment, the dialysate flow rate increases due to plasma water filtering across into the dialysate compartment as mentioned above. Upon exiting the second dialyzer cartridge, the dialysate fluid may be pumped into the first dialyzer cartridge, again running counter-parallel to the bloodside fluid. At this point, a non-isosmotic dialysate fluid may be added to the dialysate fluid, resulting in fluid which is either hypertonic or hypotonic relative to the blood. The addition of non-isosmotic fluid to the dialysate fluid may have the following effects: (a) an increase in the overall dialysate flow results in a reduction of the dialysate side-mass transport resistance; (b) a reduction in the dialysate inlet solute concentration prior to entering the first dialyzer cartridge results in an increase of the concentration gradient across the semi-permeable membrane; (c) a fluid shift across the red blood cell membrane further enhances transport of solutes out of the red blood cells; and (d) larger molecules sieved by the red blood cell membrane are trapped in the plasma water space thus increasing their concentration gradient relative to the dialysate. In an embodiment of the invention, pretreated water is used as the non-isosmotic fluid added to the dialysate fluid. This may have the added benefit of increasing dialysate flow without increasing costs associated with the amount of dialysate concentrate being used.

A sterile/non-pyrogenic substitution fluid for use in conjunction with the present invention may be prepared by drawing a portion of fresh dialysate solution from a dialysate inlet line and pumping it through a sterile filter cartridge. In an embodiment of the present invention, the sterile filter cartridge performs at least a double filtration of the dialysate solution before the solution is introduced into the blood stream as a substitution fluid. This double filtration can be performed by two separate ultrafiltration filter cartridges or a single cartridge that has multiple sections to perform multiple filtration of the substitution fluid. The use of multiple filtration to generate the on-line substitution fluid makes the system of the present invention safer, should one of the filters fail during treatment.

The dialysis machine used in conjunction with the present invention may perform all of its normal functions, such as metering dialysate flow rate, monitoring pressures, controlling net ultrafiltration, monitoring used dialysate for blood presence, etc. The hemodiafiltration device of the present invention operates in conjunction with the dialysis machine, either as part of the dialysis machine or as an add-on system, e.g., to re-distribute dialysate fluid to its respective dialyzer and sterile filter cartridges. Preparation of non-isosmotic dialysate fluid, as described in detail below, may be performed by a preparation module included in the dialysis machine. The fluid handling components of the hemodiafiltration system may be integrated with a microprocessor unit for controlling and executing the diafiltration aspect of the treatment, or a control unit of the dialysis machine may be adapted to control the hemodiafiltration aspects of the treatment.

Figure 1A:
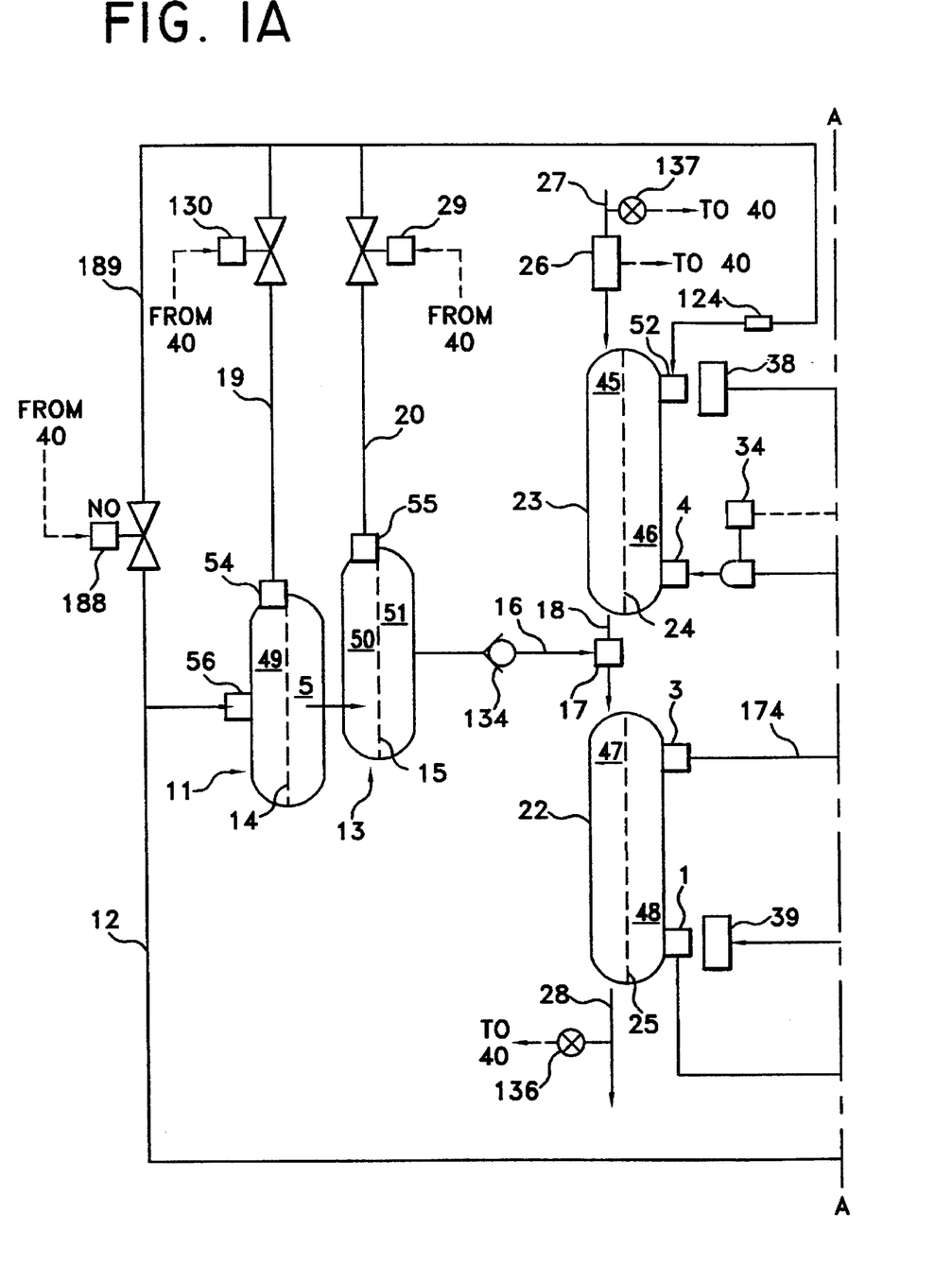
FIG. 1A is a schematic illustration of a first section of a non-isosmotic hemodiafiltration device system in accordance with an embodiment.
Figure 1B:
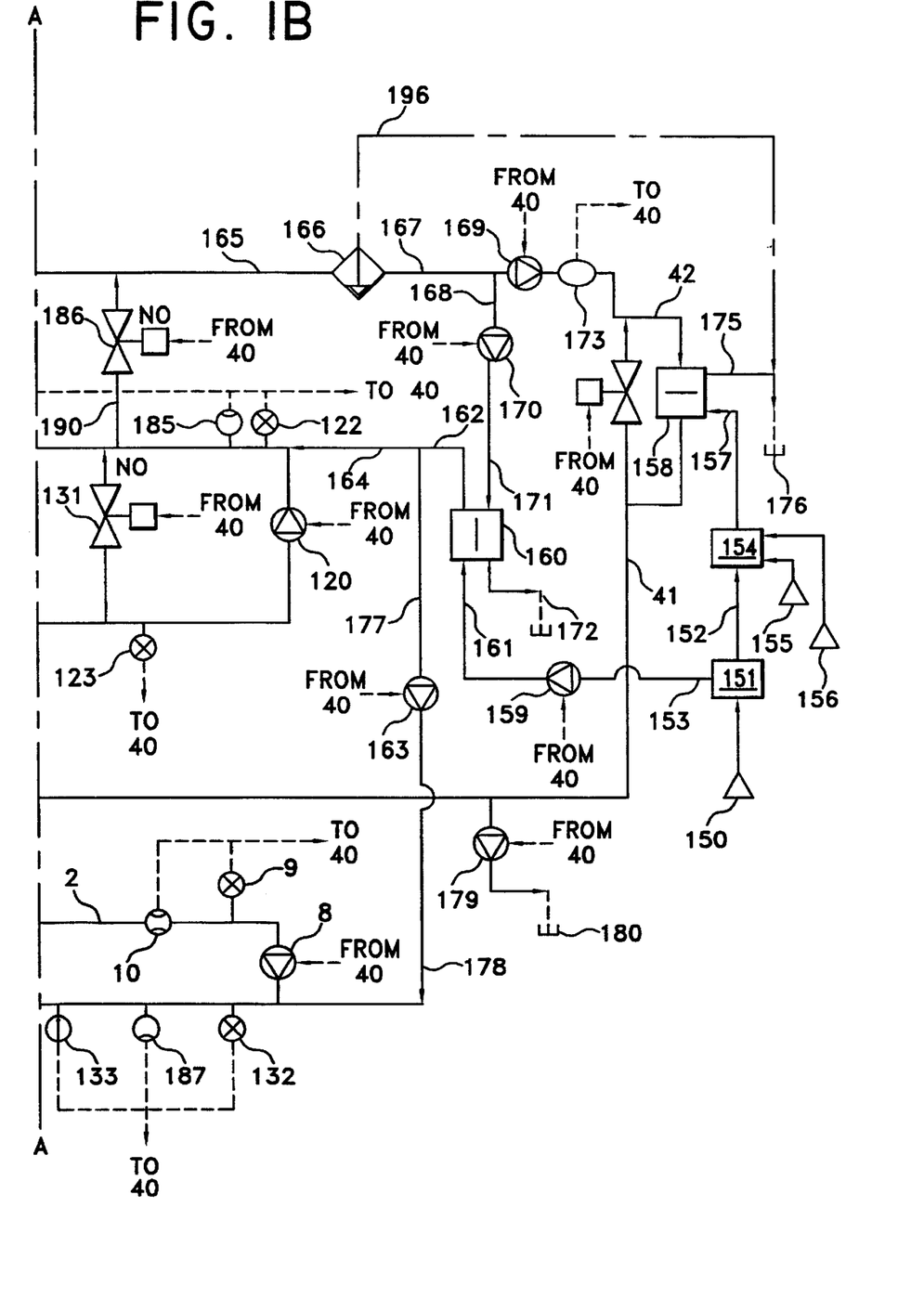
FIG. 1B is a schematic illustration of a second section of a non-isosmotic hemodiafiltration system in accordance with an embodiment.

Reference is now made to the FIG. 1, which schematically illustrates a non-isosmotic hemodiafiltration device in accordance with an embodiment of the present invention. It should be appreciated that the system of FIG. 1 demonstrates only one preferred embodiment of the invention, and that other possible configurations of the system of the present invention may be equally or even more suitable, depending on specific requirements. For example, the use of a substantially hypotonic dialysate fluid in the first dialyzer stage and a substantially hypertonic dialysate fluid in the second dialyzer stage, as described below, may be reversed in some embodiments of the invention, i.e., a substantially hypertonic dialysate fluid may be used in the first dialyzer stage and a substantially hypotonic dialysate fluid may be used in the second dialyzer stage.

In the system of FIG. 1, blood to be cleaned 27 enters a first dialyzer cartridge 23 after passing through blood monitoring devices 137 and 26. Blood monitoring devices 137 and 26 monitor the incoming blood pressure and/or the incoming blood flow rate and provide an input, responsive to the monitored rate, to a control unit 40. The blood is carried by suitable tubing, as is known in the art, for example, bloodline tubing made from flexible polyvinylchloride (PVC). The flow rate of incoming blood is generally in the range of 100 to 600 ml/min, preferably 200 to 500 ml/min.

First dialyzer cartridge 23 contains a semi-permeable membrane 24 that divides the dialyzer into a blood compartment 45 and a dialysate compartment 46. As blood 27 passes through blood compartment 45, plasma water containing blood substances is filtered across semi-permeable membrane 24. Additional blood substances are also transferred across semi-permeable membrane 24 by diffusion due to a difference in concentration between blood compartment 45 and dialysate compartment 46.

The dialyzer cartridge may be of any type suitable for hemodialysis, hemodiafiltration, hemofiltration, or hemoconcentration, for example, the Fresenius F60, available from Fresenius Medical Care, Lexington, Mass., the Baxter CT 110, available from Baxter Health Care, Deerfield, Ill., the Minntech Hemocor HPH 1000, available from Minntech Corporation, Minneapolis, Minn., or the Hospal Filtral 16, available from Hospal A.G., Switzerland. Membrane 24 is preferably a medium to high flux membrane, for example, the polysulfone, cellulose triacetate or acrylonitrile membranes available from Fresenius Medical Care, Lexington, Mass., Minntech Corporation, Minneapolis, Minn., Baxter Health Care, Deerfield, Ill., or Hospal A.G., Switzerland.

Partially diafiltered blood (denoted 18) exiting dialyzer cartridge 23 is mixed with sterile substitution fluid 16 to form a blood/substitution fluid mixture 17. This mixture enters a second dialyzer cartridge 22 containing a semi-permeable membrane 25 which divides the dialyzer cartridge 22 into a blood compartment 47 and a dialysate compartment 48. As mixture 17 passes through blood compartment 47, plasma water containing blood substances is filtered across the semi-permeable membrane. As in the first dialyzer cartridge, additional blood substances are transferred across semi-permeable membrane 25 by diffusion due to concentration gradients between the blood and dialysate compartments. Cleansed blood 28 exits second dialyzer cartridge 22 and is recycled to the patient (not shown) through suitable tubing, for example, bloodline PVC tubing, as is known in the art. The pressure of cleansed blood 28 may also be monitored by a pressure sensor 136.

The second dialyzer cartridge may be of any type suitable for hemodialysis, hemodiafiltration, hemofiltration, or hemoconcentration, for example, the Fresenius F60, available from Fresenius Medical Care, Lexington, Mass., the Baxter CT 110, available from Baxter Health Care, Deerfield, Ill., the Minntech Hemocor HPH 400, available from Minntech Corporation, Minneapolis, Minn., or the Hospal Filtral 16, available from Hospal A.G., Switzerland. Membrane 25 is preferably a medium or high flux membrane, for example, the polysulfone, cellulose triacetate or acrylonitrile membranes mentioned above with reference to membrane 24.

In accordance with an embodiment of the present invention, the dialysate solution used for the present invention may be prepared as follows. A suitable quality of water, such as reverse osmosis water as is known in the art, is provided from a water source 150. The water enters a water preparation module 151 that heats and degasses the water being used by the hemodiafiltration system. Any suitable heating and degassing module as is known in the art may be used in conjunction with the present invention. Examples of such modules are included in the following systems: the Baxter SPS1550, available from Baxter Health Care, Deerfield, Ill.; the Cobe Centry System 3, available from Cobe Labs, Lakewood, Colo.; the Fresenius A2008, available from Fresenius Medical Care, Lexington, Mass.; and the Althin System 1000, available from Althin Medical, Miami, Fla. The degassed, heated water feeds into two water supply lines, namely, water feed lines 152 and 153.

Feed line 153 supplies water to prepare a non-isosmotic substitution fluid in accordance with the present invention, as described below, and/or to increase the flow of dialysate into first dialyzer cartridge 23. Feed line 152 supplies water to a dialysate preparation module 154. In dialysate preparation module 154, water is mixed with suitable amounts of dialysate concentrates. Any suitable dialysate preparation module as is known in the art may be used in conjunction with the present invention. Examples of such modules are included in the following systems: the Baxter SPS1550, available from Baxter Health Care, Deerfield, Ill.; the Cobe Centry System 3, available from Cobe Labs, Lakewood, Colo.; the Fresenius A2008, available from Fresenius Medical Care, Lexington, Mass.; and the Althin System 1000, available from Althin Medical, Miami, Fla. The mixed dialysate fluid exiting dialysate preparation module 154 flows through a conduit 157 leading to a primary dialysate balancing module 158, which may include a fluid balancing chamber as is known in the art. Primary balancing module 158 regulates flow in the sense that flow into balancing module 158 is equal to flow out of the balancing module. This provides initial filtration control which prevents the blood from becoming over-diluted or over-concentrated when exiting dialyzer cartridge 22. Upon exiting primary balancing module 158, the dialysate fluid flows via conduit 41 to a connector 39 which connects the fluid flow to a dialysate port 1 of compartment 48 of second dialyzer cartridge 22.

In an embodiment of the present invention, preparation of a sterile substitution fluid is performed by filtration of a dialysate across at least two filter membranes with a molecular weight cut-off of not more than 40,000 Daltons. In some embodiments, the nominal molecular weight cut-off for the second filter or final filter (when more than two filters are used) is not more than 10,000 Daltons, preferably not more than 5,000 Daltons. To accomplish this, a portion of the fresh dialysate solution may be split off the dialysate fluid stream at some point prior to entering dialysate compartment 48 of second dialyzer cartridge 22. The split-off portion of the dialysate solution may flow through a conduit 2 leading to a substitution pump 8. Flow rate and pre-pump pressure in conduit 2 may be monitored by a flow meter 10 and a pressure transducer 9. Substitution fluid pump 8 generates the needed pressure to force the fluid down a conduit 12, across first and second sterile filter cartridges, 11 and 13, respectively, and into blood stream 18. En route to sterile filters 11 and 13, post-pump pressure and temperature may be monitored by a pressure transducer 132 and a temperature sensor 133.

To change the osmolality of the substitution fluid, water from a conduit 178 may be added to the substitution fluid at some point downstream of substitution fluid pump 8. The resultant osmolality of the substitution fluid is a function of the relative flow rates of substitution fluid pump 8 and a pump 163 which may be provided along water conduit 178. The mixed substitution fluid stream may be monitored for conductivity by a conductivity meter 187. If the conductivity is determined to be outside a pre-determined range, a bypass valve 188 is opened to allow substitution fluid to flow via a conduit 189 which leads to a dialysate outlet port 52 of dialysate compartment 46 of dialyzer cartridge 23.

First sterile filter cartridge 11 contains a semi-permeable membrane 14 that separates the filter cartridge into an upstream compartment 49 and a downstream compartment 5. Upstream compartment 49 has an inlet port 56 and an outlet port 54, the latter being connected to a conduit 19. Air maybe vented from upstream compartment 49, via outlet port 54 and conduit 19 upon opening of a valves 130 and a valve 29. Closing of valve 130 forces the dialysate fluid to filter (or permeate) across semi-permeable membrane 14 and into downstream compartment 5.

The filtrate from downstream compartment 5 then flows into second sterile filter cartridge 13 containing a semi-permeable membrane 15 which separates the filter cartridge into an upstream compartment 50 and a downstream compartment 51. Upstream compartment 50 has an outlet port 55 for venting air from both compartment 5 of cartridge 11 and compartment 50 of cartridge 13. Outlet port 55 is connected to a conduit 20 which is connected to the venting line between valves 130 and 29. Closing of both valves 29 and 130 forces the dialysate to filter across semi-permeable membrane 15 and into downstream compartment 51. The filtered dialysate flows out of compartment 51 and through a check valve 134, which minimizes blood back-flow into sterile filter cartridge 13.

The sterile dialysate (or substitution fluid) 16 exiting sterile filter cartridge 13 is mixed with blood exiting cartridge 23 to form the blood/substitution fluid mixture 17 described above. In some embodiments of the present invention (not shown in the drawings), a portion of substitution fluid may be added to the blood stream exiting second dialyzer cartridge 22, provided that the blood does not become overly viscous in the second dialyzer cartridge due to hemoconcentration.

During priming or flushing of sterile filter cartridges 11 and 13, valves 130 and 29 are opened to allow flow therethrough. The flow downstream of valve 29 is directed, via a suitable fluid conduit, to a junction near dialysate outlet port 52 of dialyzer cartridge 23. An air detector 124 may be placed downstream of valve 29, to ensure that air is purged from sterile filter cartridges 11 and 13 during priming.

The dialysate not used as substitution fluid enters the second dialyzer cartridge 22 through inlet port 1 of dialysate compartment 48, and flows counter-parallel to the blood flow as it traverses through compartment 48. During diafiltration, plasma water filters across semi-permeable membrane 25 and mixes with the dialysate fluid. The dialysate fluid together with the filtered plasma water exits the dialyzer cartridge, at outlet port 3, through a tubing conduit 174 which directs the fluid to a first path, including a bypass valve 131, and a second path including a pump 120. Downstream of valve 131 and pump 120, the two paths are rejoined and the combined fluid flow is connected to an inlet port 4 of dialysate compartment 46 of first dialyzer cartridge 23.

In an embodiment of the present invention, to raise the dialysate flow rate into first dialyzer cartridge 22, an additional flow of water 164 may be added to the dialysate flow stream downstream of pump 120. The addition of water flow 164 into the dialysate flow stream raises the dialysate flow rate and increases the dialysate concentration gradient in dialyzer cartridge 23. The non-isosmotic nature of the dialysate may cause a fluid shift across red cell membranes in the treated blood, thereby improving the removal of solutes from the blood.

Pressure transducers 123 and 122 monitor pre-pumping and post-pumping pressures, respectively, across pump 120, and inputs responsive to these pressures are provided to control unit 40. A flow switch 34 and a conductivity meter 185 may be placed on the line leading to dialysate inlet port 4. Flow switch 34 may be used to ensure that a minimum dialysate flow is maintained to carry out the diafiltration operation. The output of conductivity meter 185 may be used to ensure that the conductivity of the dialysate is maintained within a predetermined, acceptable range, for example, a conductivity range which yields a final dialysate sodium concentration (i.e., concentration after dilution with water) of about 70 meq/L to about 135 meq/L. Based on the output of conductivity meter 185, if the dialysate conductivity falls outside the acceptable range, opening of a bypass valve 186 directs the dialysate fluid to bypasses first dialyzer cartridge 23 via a bypass conduit 190.

During normal operation of the system, valve 131 is closed whereby all flow is diverted to pump 120. In this mode, the speed of the pump can be used to control the amount of ultrafiltration that occurs across the second dialyzer cartridge membrane 25. For example, if the rate of fluid flow pumped by pump 120 matches the inlet dialysate flow rate into compartment 48, then the net ultrafiltration of fluid across the membrane is zero. Increasing the speed of the pump to pump above the inlet dialysate flow rate results in an ultrafiltration rate equal to the difference between these two flow rates. Dialysate fluid entering first dialyzer cartridge 23 through inlet port 4 runs counter-parallel to the blood flow as it traverses through the dialysate compartment 46. Plasma water filters across semi-permeable membrane 24 of cartridge 23 into compartment 46, where the plasma water is combined with the dialysate fluid, and the combined fluid exits at dialysate outlet port 52.

The used dialysate fluid may be returned to primary balancing module 158 via a dialysate outlet line connector 38, connected to dialysate outlet port 52 of dialyzer cartridge 23, and a conduit 42. A conduit 165 carries the used dialysate from dialysate outlet connector 38 to an air trap 166. In the air trap, air is removed via a conduit 196 which leads to a drain 176. The resultant air-free, used, dialysate fluid flows through a conduit 167 where it branches to a main dialysate pump 169 and, via a conduit 168, to a secondary dialysate pump 170. Main dialysate pump 169 feeds used dialysate fluid, via a blood leak detector 173 and conduit 42, back to main balancing module 158. The used dialysate exits main balancing module 158 via a conduit 175 which leads to drain 176. A heat exchanger (not shown in the drawing) may be used to partially heat the incoming water, thereby to assist the heating function of water preparation module 151.

The used dialysate fluid not entering main balancing module 158 is pumped by secondary pump 170 via a conduit 168 to a secondary balancing module 160, which may include a fluid balancing chamber as is known in the art. The purpose of second balancing module 160 is to ensure that any additional flow of water into the dialysate fluid circuit and/or into the substitution fluid circuit, i.e., into the non-isosmotic portions of system, is balanced by a substantially equivalent removal of used dialysate fluid from those non-isosmotic circuits. The used dialysate from secondary balancing module 160 exits via a conduit 172 which leads to drain. The flow of this exiting stream is matched by the entering flow of fresh water from the water preparation module 151 via conduit 153, pump 159 and conduit 161. Fresh water 162 exiting secondary balancing module 160 branches into two water streams, namely a stream 177 which feeds water to pump 163, leading to the substitution fluid circuit, and a stream 164 which feeds water to the dialysate fluid circuit.

It will be appreciated by persons skilled in the art that the use of two dialyzer stages, as described above, enables increased dialysate flow into the first dialyzer and, thus, increased solute clearance in the first dialyzer, without increasing the cost normally associated with increased dialysate flow. This is achieved by using a substantially hypotonic dialysate in the first dialyzer stage and a substantially isotonic dialysate or slightly hypertonic in the second dialyzer stage. Isotonic or slightly hypertonic dialysate is introduced only in the second dialyzer stage to bring the substantially hypotonic blood exiting the first dialyzer stage to a desired range of isotonicity, thereby reducing the amount of isotonic dialysate used. The hypotonic dialysate used in the first stage is less expensive than the isotonic dialysate used in the second stage because the hypotonic dialysate is more diluted (i.e., contains less salts per unit volume) than isotonic dialysate. The diluted dialysate used in the first stage operates to remove salts from the blood, and these salts are replaced by salts from the more concentrated dialysate used in the second stage.

Figure 2:
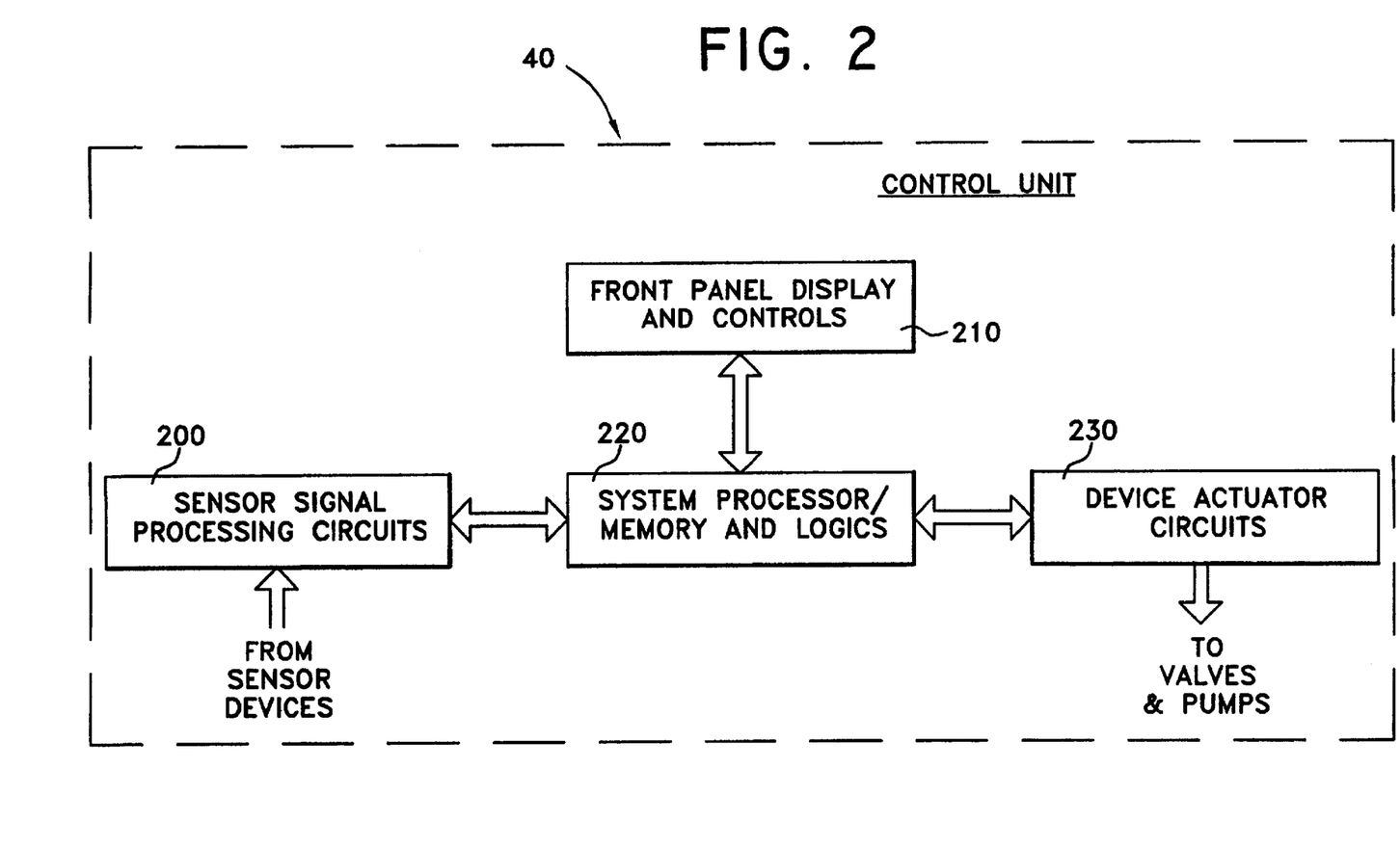
FIG. 2 is a schematic illustration of a control unit for monitoring and controlling the operation of the hemodiafiltration system of FIG. 1 in accordance with an embodiment of the present invention.

Reference is now made also to FIG. 2 which schematically illustrates an embodiment of control unit 40. Control unit 40 may include a processor 220 which monitors and controls the operation the hemodiafiltration system. As shown more specifically in FIG. 1, control unit 40 receives inputs from various components of the hemodiafiltration device, e.g., from pressure transducers, flow meters, conductivity meters, flow switches, etc., as described above. These inputs may be processed by sensor signal processing circuits 200, which may include analog-to-digital (D/A) converters and other circuits as are known in the art, providing an input which is readable by processor 220. Using suitable control hardware and/or software, for example, device actuator circuits 230 as shown in FIG. 2, control unit 40 controls various system functions, such as setting values for pump speeds, opening/closing valves. Various system parameters, calculated based on the inputs may be displayed on a display 210 of control unit 40.

While certain specific embodiments of the invention are disclosed as typical, the invention is not limited to these particular forms, but rather is applicable broadly to all such variations as fall within the scope of the appended claims. To those skilled in the art to which the invention pertains many modifications and adaptations will occur. Thus, the specific structures and methods discussed in detail above are merely illustrative of specific embodiments of the invention.

What is claimed is:

1. In a blood cleansing system, a hemodiafiltration device comprising:
   a first dialyzer including:
      a first semi-permeable membrane partitioning said first dialyzer into:
         a first blood compartment having a first blood inlet which receives blood to be cleaned and a first blood outlet which discharges at least partially diafiltered blood, the blood received within the first blood inlet being in an isosmotic state; and
         a first dialysate compartment having a first dialysate inlet and a first dialysate outlet;
   a second dialyzer including:
      a second semi-permeable membrane partitioning said second dialyzer into:
         a second blood compartment having a second blood inlet receives the partially diafiltered blood and a second blood outlet which discharges diafiltered blood;
         a second dialysate compartment having a second dialysate inlet and a second dialysate outlet; and
   a first dialysate fluid supply which supplies a first non-isosmotic dialysate fluid through a first conduit to the first dialysate inlet of said first dialyzer causing the blood discharged from the first blood outlet to be in a non-isosmotic state, and a second dialysate fluid supply which supplies a second dialysate fluid through a second conduit to the second dialysate inlet of said second dialyzer, the second dialysate fluid having an osmolarity opposite that of the first non-isosmotic dialysate fluid so that the blood being discharged from the second blood outlet is returned substantially to the isosmotic state.

2. A hemodiafiltration device according to claim 1 wherein each of said first and second dialysate fluid supplies comprises:
   a water preparation module which provides a supply of water;
   a source of dialysate fluid concentrate; and
   a dialysate fluid preparation module which mixes said supply of water with a predetermined amount of dialysate fluid concentrate to produce one of said first and second dialysate fluids.

3. A hemodiafiltration device according to claim 1 wherein said first non-isosmotic dialysate fluid comprises hypotonic dialysate fluid.

4. A hemodiafiltration device according to claim 1 wherein said first non-isosmotic dialysate fluid comprises hypertonic dialysate fluid.

5. In a blood cleansing system, a hemodiafiltration device comprising:
   a first dialyzer including:
      a first semi-permeable membrane partitioning said first dialyzer into:
         a first blood compartment having a first blood inlet which receives blood to be cleaned and a first blood outlet which expels partially diafiltered blood; and
         a first dialysate compartment having a first dialysate inlet and a first dialysate outlet;
   means for mixing said partially diafiltered blood with substitution fluid from a source of substitution fluid to obtain a blood/substitution fluid mixture;
   a second dialyzer including:
      a second semi-permeable membrane partitioning said second dialyzer into:
         a second blood compartment having a second blood inlet which receives said blood/substitution fluid mixture and a second blood outlet which expels diafiltered blood; and
         a second dialysate compartment having a second dialysate inlet and a second dialysate outlet;
   a first dialysate fluid supply which supplies non-isosmotic dialysate fluid through a conduit to said first dialysate inlet;
   a second dialysate fluid supply which supplies a second dialysate fluid through a conduit to said second dialysate inlet; and
   a control unit which controls the flow of blood through said first and second dialyzers and the flow of dialysate fluid through said first and second dialysate compartments.

6. A hemodiafiltration device according to claim 5 wherein said first and second dialyzers comprise first and second cartridges, respectively.

7. A hemodiafiltration device according to claim 5 wherein said non-isosmotic dialysate fluid comprises hypotonic dialysate fluid.

8. A hemodiafiltration device according to claim 5 wherein said non-isosmotic dialysate fluid comprises hypertonic dialysate fluid.

9. A method of hemodiafiltration comprising the steps of:
   supplying a blood inflow;
   diafiltering said blood inflow using a first non-isosmotic dialysate fluid to provide a partially diafiltered blood outflow;
   mixing said partially diafiltered blood outflow with a substitution fluid to provide a blood/substitution fluid mixture; and
   diafiltering said blood/substitution fluid mixture using a second non-isosmotic dialysate fluid.

10. A method according to claim 9 wherein the step of diafiltering said blood inflow comprises the step of diffusing a portion of said blood inflow into a countercurrent of said first non-isosmotic dialysate fluid, and wherein the step of diafiltering said blood/substitution fluid mixture comprises the step of diffusing a portion of said blood/substitution fluid mixture by a countercurrent of said second non-isosmotic dialysate fluid.

11. A method according to claim 9 wherein the first non-isosmotic dialysate fluid comprises a hypotonic dialysate fluid and wherein said second non-isosmotic dialysate fluid comprises a hypertonic dialysate fluid.

12. A method according to claim 9 wherein said first non-isosmostic fluid comprises a hypertonic dialysate fluid and wherein said second non-isosmotic dialysate fluid comprises a hypotonic dialysate fluid.

13. A method according to claim 10 wherein said first non-isosmotic dialysate fluid comprises a hypotonic dialysate fluid and wherein said second non-isosmotic dialysate fluid comprises a hypertonic dialysate fluid.

14. A method according to claim 10 wherein said first non-isosmotic dialysate fluid comprises a hypertonic dialysate fluid and wherein said second non-isosmotic dialysate fluid comprises a hypotonic dialysate fluid.

15. In a blood cleansing system, a hemodiafiltration device comprising:
   a first dialyzer including:
      a first semi-permeable membrane partitioning said first dialyzer into a first blood compartment and a first dialysate compartment, said first blood compartment having a first blood inlet for receiving blood to be cleaned and a first blood outlet for discharging blood having a first concentration of toxins, the blood received through the first blood inlet being in an isosmotic state, said first dialysate compartment having a first dialysate inlet and a first dialysate outlet;
   a second dialyzer including:
      a second semi-permeable membrane partitioning said second dialyzer into a second blood compartment and a second dialysate compartment, said second blood compartment having a second blood inlet for receiving the blood having the first concentration of toxins and a second blood outlet for discharging blood having a second concentration of toxins, wherein the second concentration is less than the first concentration, said second dialysate compartment having a second dialysate inlet and a second dialysate outlet;
   a first dialysate fluid supply which supplies a first non-isosmotic dialysate fluid through a first conduit to said first dialysate inlet of said first dialyzer such that the blood discharged from the first blood outlet being in a non-isosmotic state; and
   a second dialysate fluid supply which supplies a second dialysate fluid through a second conduit to said second dialysate inlet of said second dialyzer, the second dialysate fluid having an osmolarity opposite that of the first non-isosmotic dialysate fluid so that the blood being discharged from the second blood outlet is returned substantially to the isosmotic state.

16. A hemodiafiltration device according to claim 15 wherein said first non-isosmotic dialysate fluid comprises a hypotonic dialysate fluid.

17. A hemodiafiltration device according to claim 15 wherein said first non-isosmotic dialysate fluid comprises a hypertonic dialysate fluid.

18. A hemodiafiltration device according to claim 15 wherein each of said first and second dialysate fluid supplies comprises:
   a water preparation module which provides a supply of water;
   a source of dialysate fluid concentrate; and
   a dialysate fluid preparation module which mixes said supply of water with a predetermined amount of dialysate fluid concentrate to produce one of said first and second dialysate fluids.

19. A method of hemodiafiltration comprising the steps of:
   supplying a blood inflow, the blood inflow being in an isosmotic state;
   diafiltering said blood inflow with a first non-isosmotic dialysate fluid to provide a first blood outflow having a first concentration of toxins and being in a non-isosmotic state; and
   diafiltering said first blood outflow with a second dialysate fluid to provide a second blood outflow having a second concentration of toxins, wherein the second concentration is less than the first concentration and wherein the second dialysate fluid has an osmolarity opposite that of the first non-isosmotic dialysate fluid so that the blood being discharged from the second blood outlet is returned substantially to the isosmotic state.

20. A method according to claim 19 wherein said first non-isosmotic dialysate fluid comprises a hypotonic dialysate fluid.

21. A method according to claim 19 wherein said first non-isosmotic dialysate fluid comprises a hypertonic dialysate fluid.

22. In a blood cleansing system, a hemodialysis device comprising:
   a first dialyzer including:
      a first semi-permeable membrane partitioning said first dialyzer into a first blood compartment and a first dialysate compartment, said first blood compartment having a first blood inlet for receiving blood to be cleaned and a first blood outlet for discharging blood having a first concentration of toxins, the blood received through the first blood inlet being in an isosmotic state, said first dialysate compartment having a first dialysate inlet and a first dialysate outlet;
   a second dialyzer including:
      a second semi-permeable membrane partitioning said second dialyzer into a second blood compartment and a second dialysate compartment, said second blood compartment having a second blood inlet for receiving the blood from the first dialyzer and a second blood outlet for discharging blood having a second concentration of toxins, wherein the second concentration is less than the first concentration, said second dialysate compartment having a second dialysate inlet and a second dialysate outlet;
   a first dialysate fluid supply which supplies a first non-isosmotic dialysate fluid through a first conduit to said first dialysate inlet of said first dialyzer such that the blood discharged from the first blood outlet is in a non-isosmotic state; and
   a second dialysate fluid supply which supplies a second dialysate fluid through a second conduit to said second dialysate inlet of said second dialyzer, the second dialysate fluid having an osmolarity opposite that of the first non-isosmotic dialysate fluid so that the blood being discharged from the second blood outlet is returned substantially to the isosmotic state.

23. A method of hemodialysis comprising the steps of:
   supplying a blood inflow, the blood inflow being in an isosmotic state;
   dialyzing said blood inflow with a first non-isosmotic dialysate fluid to provide a first blood outflow having a first concentrations of toxins, the first blood outflow being in a non-isosmotic state; and
   dialyzing said blood outflow from said first dialyzer with a second dialysate fluid to provide a second blood outflow having a second concentration of toxins, the second concentration of toxins being less than the first concentration of toxins, the second dialysate fluid having an osmolarity opposite that of the first non-isosmotic dialysate fluid so that the second blood outflow is returned substantially to the isosmotic state.

* * * * *